ically hazardous and may lead to incontrollable runaway reactions (F. Stoessel, J. Loss Prev. Process Ind., Vol 6, No 2, 79 (1993)).

United States Patent
Baumeister et al.

(10) Patent No.: US 6,258,982 B1
(45) Date of Patent: Jul. 10, 2001

(54) PROCESS FOR THE PREPARATION OF SUBSTITUTED AROMATIC AMINO COMPOUNDS

(75) Inventors: Peter Baumeister, Flüh; Urs Siegrist, Eiken; Martin Studer, Basel, all of (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/254,586

(22) PCT Filed: Sep. 19, 1997

(86) PCT No.: PCT/EP97/05151

§ 371 Date: Mar. 10, 1999

§ 102(e) Date: Mar. 10, 1999

(87) PCT Pub. No.: WO98/13331

PCT Pub. Date: Apr. 2, 1998

(30) Foreign Application Priority Data

Sep. 23, 1996 (CH) .................................................. 2323/96

(51) Int. Cl.[7] .................................................. C07C 233/00
(52) U.S. Cl. ..................... 564/164; 564/165; 564/416; 564/417; 564/418; 564/423; 562/433; 562/452; 562/456; 560/47; 560/19; 560/20
(58) Field of Search .................................. 564/164, 165, 564/416, 417, 418, 423; 562/433, 452, 456; 560/47, 19, 20

(56) References Cited

U.S. PATENT DOCUMENTS

| 3,666,813 | 5/1972 | Hindin et al. | 260/580 |
|---|---|---|---|
| 3,944,615 | 3/1976 | Iqbal | 260/580 |
| 4,020,107 | 4/1977 | Kosak | 260/580 |
| 4,212,824 | 7/1980 | Seagraves | 260/580 |
| 5,856,578 | 1/1999 | Siegrist et al. | 564/423 |

FOREIGN PATENT DOCUMENTS

| 2 042 368 | 4/1971 | (DE) . |
| 2 214 056 | 10/1973 | (DE) . |
| 25 19 838 | 11/1976 | (DE) . |
| 28 49 002 | 5/1980 | (DE) . |
| 0 002 308 | 6/1979 | (EP) . |
| 799871 | 8/1958 | (GB) . |
| 95 32941 | 12/1995 | (WO) . |
| 95 32952 | 12/1995 | (WO) . |

OTHER PUBLICATIONS

Miller, J.A., "Carcinogenesis by Chemicals: An Overview—G. H. A. Clowes Memorial Lecture," Cancer Research, vol. 30, 1970, pp. 559–576.
Stoessel, F., "Experimental study of thermal hazards during the hydrogenation of aromatic nitro compounds," J. Loss Prev. Process Ind., vol. 6, No. 2, 1993, pp. 79–85.
Tong et al., "3–4–Dichloroaniline Autoclave Incident," AICHE Loss Prev., vol. 11, 1977, pp. 71–75.
Kosak, J.R., "Hydrogenation of Nitroarenes—The Hydroxylamine Intermediate," Catalysis of Organic Reactions, Dec. 1988, pp. 135–147.
Kosak, J.R., Catalysis in Organic Synthesis, 1980, pp. 107–117.
Marino, J.P. et al. Synthetic Communications, vol. 24, No. 6, 1994, pp. 839–848.
Rylander, P.N., Hydrogenation Methods, Academic Press, London, 1985, pp. 326–329.
Rylander, P.N., Catalytic Hydrogenation in Organic Synthesis, Academic Press, London, 1979, p. 140.
Rylander, P.N., Hydrogenation Methods, Academic Press, London, 1985, p. 77.
Freifelder, M., Practical Catalytic Hydrogenation, Wiley, New York, 1971, p. 256.
Freifelder, M., Practical Catalytic Hydrogenation, Wiley, New York, 1971, pp. 306–306.
Derwent Abstract, 86–046753 (1986) of SU 285689A.
Chem. Abstr. vol. 76:104258a (1972) of Bizhanov, et al.

*Primary Examiner*—Samuel Barts
(74) *Attorney, Agent, or Firm*—Wenderoth, Lind & Ponack, L.L.P.

(57) ABSTRACT

The present invention relates to a hydrogenation process for the preparation of aromatic amino compounds containing directly on the aryl ring or in a side chain one or more entities that may also undergo hydrogenation, such as carbon multiple bonds, nitrile groups, imino groups or carbonyl groups. The preparation is carried out by catalytic hydrogenation of the corresponding aromatic nitro compounds in the presence of a phosphorus-modified noble metal catalyst. The invention relates also to the use of modified noble metal catalysts for the hydrogenation of aromatic nitro compounds containing carbon multiple bonds and/or substituted by nitrile, imino or carbonyl groups.

41 Claims, No Drawings

PROCESS FOR THE PREPARATION OF SUBSTITUTED AROMATIC AMINO COMPOUNDS

This application is a 371 of PCT/EP97/05151 filed Sep. 19, 1997.

This appliction is a 371 of PCT/EP 97/05/157 The present invention relates to a hydrogenation process for the preparation of aromatic amino compounds containing directly on the aryl ring or in a side chain one or more entities that may also undergo hydrogenation, such as carbon multiple bonds, nitrile groups, imino groups or carbonyl groups. The preparation is carried out by catalytic hydrogen cation of the corresponding aromatic nitro compounds in the presence of a phosphorus-modified noble metal catalyst The invention relates also to the use of modified noble metal catalysts for the hydrogenation of aromatic nitro compounds containing carbon multiple bonds and/or substituted by nitrile, imino or carbonyl groups.

It is known that aromatic nitro compounds can be reduced in the presence of noble metal catalysts and hydrogen to aromatic amines with very good Yields. When further hydrogen-ateable groups, for example carbon multiple bonds, nitrile, imino or carbonyl groups, are present at the same time, special measures are required in order to prevent the formation of undesirable secondary products, which otherwise can be separated from the desired product often only by resource-intensive means or, in especially unfavourable cases, not at all. Selective reduction is especially difficult when several hydrogenateable groups are present in a compound.

The prior art contains a number of proposals for the selective reduction of aromatic nitro compounds substituted by hydrogenateable groups. For example, WO 95/32941 and WO 95/32952 describe a process for the hydrogenation of aromatic nitro compounds that are substituted by at least one group having a carbon multiple bond. Noble metal catalysts modified with lead, mercury, bismuth, germanium, cadmium, arsenic, antimony, silver or gold are proposed as catalysts. Although those catalysts are very suitable in principle and can also be used on a production scale, occasional disadvantages emerge in respect of their activity and selectivity.

U.S. Pat. No. 4,020,107 proposes phosphorous acid, hypophosphorous acid or derivatives thereof as additives when aromatic nitro compounds halo-substituted on the aromatic moiety are hydrogenated using Pt or Pd/active carbon and hydrogen.

Although those systems are selective in respect of the halogen substituents present in the molecule, they frequently have a limited reactivity. In many cases, therefore, the formation of considerable amounts of aryl hydroxylamine is observed (J. R. Kosak, in Catalysis of Organic Reactions, Vol 18, (1988), 135–147; idem, in Catalysis in Organic Synthesis, 1980, 107–117).

Catalytic hydrogenations of aromatic nitro compounds to the corresponding aromatic amines proceed via several intermediates. The corresponding nitroso compounds and especially the hydroxylamine intermediate are of importance therein, as described, for example, by M. Freifelder in Handbook of Practical Catalytic Hydrogenation, published by Wiley-lnterscience, New York, 1971.

That hydroxylamine intermediate represents a particular problem in practice because it can, under certain conditions, accumulate in large amounts in the reaction solution. That is true especially of aromatic nitro compounds, the hydrogenation of which produces relatively stable aryl hydroxylamines, and is especially critical when the hydrogenation is carried out in a slurry batch reactor. In an extreme case, several tonnes of aryl hydroxylamine can be formed in that way.

The accumulation of aryl hydroxyiamines is undesirable in many respects. For example, it is known that such compounds are often thermally unstable and when heated, with or without $H_2$, can undergo disproportionation with marked emission of heat. The heat being released can trigger further decomposition reactions which may then result in incidents involving serious explosions. W. R. Tong et aL., AICHE Loss Prev. 1977, (11), 71–75 describe such an incident in the reduction of 3,4-dichloro nitrobenzene to 3,4-dichloroaniline.

That instability makes a detailed and resource-intensive thermal study of hydrogenation mixtures indispensable before commencing production. The thermal characteristics of the potential hydroxylamine intermediates especially must be thoroughly studied. F. Stoessel, J. Loss Prev. Process Ind., 1993, Vol 6, No. 2, 79–85 describes that procedure using the example of the hydrogenation of nitrobenzene to aniline.

Furthermore, aryl hydroxylamines are known to be powerful carcinogens and therefore represent a major potential hazard in the event of the hydrogenation being discontinued or being incomplete (J. A. Miller, Cancer Res. 3 (1970), 559).

A third problem area is the preparation of a pure amine. If there are significant amounts of aryl hydroxylamine present during the hydrogenation or at the end of the reaction, that may result in fusions, with undesirable, coloured azo or azoxy products being formed. Since the amount of aryl hydroxylamine may differ from batch to batch, a product quality is obtained that varies in purity and appearance.

The problems mentioned hereinbefore are made even more acute by the fact that neither the concentrations being formed nor even the maximum possible concentrations of that hydroxylamine intermediate can be predicted, even for well known and well studied processes. The presence of impurities in the trace range may trigger the spontaneous accumulation of hydroxylamine intermediates in an unpredictable manner. For example, J. R. Kosak in Catalysis of Organic Reactions, Vol 18, (1988), 135, describes how, in the hydrogenation of 3,4-dichloronitrobenzene, the addition of merely 1% $NaNO_3$ increases the accumulation from an initial <5% to about 30%.

It has now been found, surprisingly, that the catalytic hydrogenation of aromatic nitro compounds containing directly on the aryl ring or in a side chain one or more entities that may also undergo hydrogenation, such as carbon multiple bonds, nitrile groups, imino groups or carbonyl groups, can be carried out selectively when rhodium, ruthenium, iridium, platinum or palladium catalysts modified with an inorganic or organic phosphorus compound having an oxidation state of less than 5 are used.

Contrary to expectations, it has been shown that, using those catalyst systems, aromatic nitro compounds can be reduced selectively to the corresponding amino compounds, without the unsaturated carbon, —CN or —CO bonds of the substituents on the aromatic nitro compound being hydrogenated at the same time.

Surprisingly, in many cases only low concentrations of hydroxylamine are formed. In cases where relatively large amounts of hydroxylamine are to be expected, however, that hydroxylamine formation can be virtually completely suppressed by adding catalytic amounts of a co-catalyst, for example a vanadium compound. Usually, hydroxylamine concentrations of less than 1% are observed. As a result, it is now possible to use relatively high concentrations of aromatic nitro compounds, which contributes to the process being carried out in an extremely economic manner.

The activity and selectivity of the catalyst systems is high, especially in the case of very sensitive compounds, such as, for example, propargyi nitrobenzoate.

The catalyst systems can be readily prepared from well known and commercially available standard noble metal catalysts, such as standard Pt or Pd catalysts, so that a constant catalyst quality is assured, which is important for large-scale production.

Since no further heavy metal compounds are required for the modification, there is also no possibility of the end products being contaminated with heavy metals.

It is often possible to use a low pressure (about 5 bar) and a relatively low temperature (about 100° C.) in the hydrogenation.

A further advantage of the process over known reduction methods, such as, for example, the Bechamp or sulfide reduction, lies in the fact that no Fe sludges and no acidic or sulfur-containing waste waters, which require disposal, are formed. The product is obtained with a high degree of purity, since virtually no azo or azoxy compounds are formed and the reaction can be performed in conventional reactors, without having to use special materials. The hydrogenation, especially the concluding phase, proceeds rapidly. As a result, considerable advantages with respect to consistency of quality and economy are obtained.

The process has a high degree of operational reliability, since hydroxylamine formation can be virtually suppressed, if necessary by adding a co-catalyst.

The invention relates to a process for the preparation of substituted aromatic amino compounds containing at least one carbon-carbon, carbon-nitrogen or carbon-oxygen multiple bond on the aromatic moiety or in a side chain, by means of catalytic hydrogenation of corresponding substituted aromatic nitro compounds in the presence of a modified noble metal catalyst, wherein the noble metal catalyst used is rhodium, ruthenium, iridium, platinum or palladium modified with an inorganic or organic phosphorus compound having an oxidation state of less than 5. The noble metal catalyst used is preferably platinum or palladium, especially platinum.

The noble metal catalyst is preferably used in an amount of from 0.1 to 10% by weight, especially in an amount of from 0.5 to 2% by weight, based on the aromatic nitro compound used.

A noble metal catalyst containing from 1 to 10% by weight platinum is preferably used. The platinum that is suitable for the modification can be used in the form of platinum black, platinum oxide or, preferably, in metallic or oxidised form applied to a carrier. Especially suitable carriers are active carbon, silicon dioxide in the form of silicic acid or silica gel, aluminium oxide, calcium carbonate, calcium phosphate, calcium sulfate, barium sulfate, titanium oxide, magnesium oxide, iron oxide, lead oxide, lead sulfate and lead carbonate, with special preference being given to active carbon, aluminium oxide and silicon dioxide. Platinum applied to an afore-mentioned carrier material is commercially available or can be prepared according to methods familiar to the person skilled in the art, as have been disclosed, for example, in DE-OS-2 042 368.

In principle, it is possible to use as modifiers any inorganic or organic phosphorus compounds in which the phosphorus has an oxidation state of less than 5. Examples of derivatives of phosphorous acid are mentioned in U.S. Pat. No. 4,020,107.

Examples of further phosphorus compounds that are suitable according to the invention are phosphines $P(R_a)_{3-n}(H)_n$, phosphites $P(OR_a)_3$, phosphinous acids $HO—P(H)_m(R_a)_{2-m}$, phosphine oxides $O=P(R_a)_{3-n}(H)_n$, hypophosphonous acids

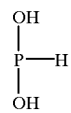

and

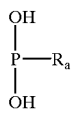

hypophosphorous acids $O=P(OH)(H)_m(R_a)_{2-m}$ and phosphorous acids $O=P(OH)_2H$ and $O=P(OH)_2R_a$, wherein $R_a$ is linear or branched $C_1$–$C_{12}$alkyl, $C_6$–$C_{16}$aryl or $C_4$–$C_{16}$heteroaryl, m is 0, 1 or 2 and n is 0, 1, 2 or 3.

Examples of $C_1$–$C_{12}$alkyl are methyl, ethyl, and the various isomers of propyl, butyl, pentyl, hexyl, heptyl, octyl, nonyl, decyl, undecyl and dodecyl.

$C_6$–$C_{16}$lAryl may be unsubstituted or substituted phenyl, naphthyl, anthracyl, 1,2,3,4-tetra-hydronaphthalene, indene, azulene or biphenyl.

$C_4$–$C_{16}$eHeteroaryl is, for example, unsubstituted or substituted quinoline, isoquinoline, pyridine, pyrimidine, pyrazine, indole, thiazole, pyrazole, oxazole, imidazole or fluorenone.

$R_a$ is preferably $C_1$–$C_6$alkyl, or phenyl that is unsubstituted or substituted by $C_1$–$C_6$alkyl or by $C_1$–$C_6$alkoxy.

The phosphorus compounds, insofar as they are acids, may be present in the form of free acids, salts, esters or amides.

Preference is given to diphenylphosphine, triphenylphosphine, phosphinous acid and salts, amides and esters thereof, diphenylphosphinic acid, diphenylphosphite, phosphine oxides, phosphorous acid and salts and esters thereof, hypophosphorous acid and salts, amides and esters thereof.

Special preference is given to phosphorous acid and salts, amides and esters thereof and to hypophosphorous acid and salts, amides and esters thereof.

As salts there should preferably be mentioned those having cations from the group of alkali and alkaline earth metals or the ammonium cation.

Preferred alkali and alkaline earth metals are Li, Na, K, Ca and Mg.

The ammonium cation can be $NH_4^+$, $(C_1-C_6alkyl)_4N^+$ or an ammonium cation substituted by a mixture of H and $C_1-C_6alkyl$.

Examples of $C_1-C_6alkyl$ are methyl, ethyl, and the various isomers of propyl, butyl, pentyl and hexyl.

The modification of the noble metal catalysts can, in principle, be carried out during or subsequent to the process for the preparation of the hydrogenation catalyst. Preferably, however, it is carried out before the addition of catalyst to the reaction mixture, or it is carried out directly in the reaction mixture by adding the phosphorus compound separately, in either dissolved or dispersed form, and stirring both components together with the solution to be hydrogenated. It is also possible during the modification to adjust the pH of the catalyst mixture to a specified value by adding acids or bases. It is likewise possible to modify the noble metal catalyst with the phosphorus compound first of all, by mixing both together as solids or by dissolving the phosphorus compound in a solvent, slurrying the noble metal catalyst with the solution and then filtering. The modified catalyst can be stored and, when required, added to the solution to be hydrogenated.

Preferably, the modification of the noble metal catalyst with the phosphorus compound is carried out before the catalytic hydrogenation.

The phosphorus compound may be soluble in the reaction medium to be hydrogenated or may be dispersed therein.

The ratio of noble metal catalyst to the modifying phosphorus compound is preferably from 1:0.1 to 1:1000, especially from 1:5 to 1:200, parts by weight.

In a preferred embodiment of the process, a catalytic amount of a co-catalyst is additionally added. In many cases where an accumulation of aryl hydroxylamine is expected, the addition of the co-catalyst can effectively prevent that accumulation.

Suitable co-catalysts are transition metal ions that are purely inorganic or optionally bound in a complex with organic ligands. The co-catalysts can either be dissolved in the reaction medium or applied to a carrier material, to the catalyst or to the modified catalyst.

Preferred transition metal ions are $Fe^{2+}$, $Fe^{3+}$, $Ru^{3+}$, $Mn^{2+}$, $Mn^{3+}$, $Co^{2+}$, $Co^{3+}$ and vanadium compounds in which the vanadium has the oxidation state 0, II, III, IV or V.

Special preference is given to elemental vanadium or vanadium compounds in which the vanadium has the oxidation state 0, II, III, IV or V.

The co-catalysts can be dissolved or dispersed in catalytic amounts in the reaction medium.

In another, likewise preferred embodiment of the process, the vanadium compound is mixed with, or applied to, the noble metal catalyst. The noble metal catalyst can have been modified with the phosphorus compound already or can be modified therewith only subsequently. The vanadium compound can, in principle, also be applied to the hydrogenation catalyst in the course of its preparation process, before or after the modification with a phosphorus compound.

Preference is also given to first of all applying the vanadium compound to a suitable carrier material and dispersing it in that form in the reaction medium. Suitable carrier materials are, for example, any carrier materials used for the preparation of commercially available, powdered hydrogenation catalysts, as mentioned hereinbefore. Active carbon is especially suitable.

Application to the catalyst or the carrier material is carried out by simple means, for example by dissolving the vanadium compounds, slurrying the catalyst or the carrier material in the solution and then filtering.

During application of the vanadium compound the pH of the slurry is adjusted, if necessary, to the desired value by adding acids or bases.

If the vanadium compounds are not soluble in the reaction medium, they can also be mixed in dispersed, slurried form with the slurried catalyst and filtered off together.

Suitable vanadium compounds having the oxidation state 0, II, III, IV or V are elemental vanadium and purely inorganic compounds, and also organic complexes with, for example, oxalate and acetylacetonate.

Preference is given to vanadium compounds such as $V_2O_5$, $V_2O_4$, vanadium(III) acetyl-acetonate, vanadium(IV) oxyacetylacetonate and those in the form of a purely inorganic salt, oxo salt or the hydrate of a purely inorganic salt or oxo salt. Examples are $VOCl_3$, $VCl_6^-$, $[VO(SCN)_4]^{2-}$, $VOS_4$, $NH_4VO_3$, $VCl_3$, $VOCl$, $VCl_2$ and the corresponding halides with F or Br. The compounds are present in aqueous solution in various forms of hydrate depending on the pH value (F. A. Cotton, G. Wilkinson, Anorganische Chemie, Veriag Chemie Weinheim 1968, 2nd edition, pages 757–766).

Special preference is given to the vanadates or the hydrates of vanadates having the oxidation state V, to vanadium(III) acetylacetonate and to vanadium(IV) oxyacetylacetonate, especially to vanadium(III) acetylacetonate and vanadium(IV) oxyacetylacetonate.

Among the vanadates preference is given to the ammonium, lithium, sodium or potassium vanadates and to hydrates of those vanadates.

The vanadium compound is used preferably in an amount of from 1 to 2000 ppm, especially in an amount of from 5 to 1000 ppm, based on the aromatic nitro compound to be hydrogenated.

The ratio by weight of vanadium compound to noble metal catalyst is preferably from 1:1 to 1:10 000, especially from 1:10 to 1:1000, and more especially from 1:50 to 1:750.

The process according to the invention is carried out preferably at a pressure of from 1 to 100 bar, more preferably at a pressure of from 1 to 40 bar, and especially at a pressure of from 1 to 5 bar.

The temperature may be from 0° to +160° C. and is preferably from +20° to +140° C. and especially from +20° to +100° C.

If the compound to be hydrogenated is liquid at the reaction temperature, the hydrogenation can be carried out without a solvent or, if the resulting amino compound is liquid under reaction conditions, that can be used as solvent.

It is, however, also possible to add solvents. Suitable solvents are, for example, water, alcohols, such as methanol, ethanol, n-propanol, iso-propanol, n-butanol, the various isomers of butanol and cyclohexanol, ethers, esters and ketones, for example diethyl ether, methyl tert-butyl ether, tetrahydrofuran, dioxane, dimethoxyethane, ethyl acetate, butyl acetate, butyrolactone, acetone, methyl ethyl ketone, methyl isobutyl ketone and cyclohexanone, carboxylic acids, such as acetic acid and propionic acid, dipolar, aprotic solvents, such as dimethyformamide, N-methylpyrrolidone, dimethylacetamide, sulfolane, dimethyl sulfoxide andacetonitrile, apolar solvents, such as toluene and xylene, chlorinated aromatic hydrocarbons, such as methylene chloride, $C_3$–$C_7$alkanes and cyclohexane.

Those solvents may be used in pure form or in the form of mixtures. In especially preferred embodiments of the process according to the invention, there are used as solvent tetrahydrofuran, toluene or xylene in pure form or in the form of mixtures with the solvents mentioned hereinbefore, especially with alcohols and/or $C_1$–$C_4$carboxylic acids.

When solvents are used, the concentration of aromatic nitro compound in the solution is preferably from 5 to 50% by weight, especially from 10 to 30% by weight.

The reaction according to the invention is carried out preferably in the liquid phase, especially using a powdered catalyst either continuously or discontinuously as semi-solid phase hydrogenation or in a bubble column or using a shaped catalyst in a trickle bed. Furthermore, the reaction can be carried out in the gas phase using a powdered catalyst in a fluid bed or using a shaped catalyst in a fixed bed.

The unsaturated carbon-carbon bonds referred to in the present invention include alkene, alkyne and allene bonds.

Compounds having —CN multiple bonds are, for example, oximes, imines, isocyanates, isocyanurates, hydrazones, azines and nitrites. They can either be bonded directly to the aromatic moiety or can be present as substituents in a side chain. Preferred groups are nitriles, imines, oximes and hydrazones.

Compounds having —CO multiple bonds are, for example, aldehydes or ketones, for example arylalkyl ketones or quinones. The CO bonds can be bonded directly to the aromatic nitro moiety or be in a side chain.

The side chains may be aliphatic, cycloaliphatic, aromatic, heteroaromatic, mixed aliphatic-cycloaliphatic, aromatic-aliphatic or heteroaromatic-aliphatic side chains.

The process is also suitable for a case where CC— and —CN multiple bonds, carbonyl and halogen groups are simultaneously present as substituents in the whole molecule or in the side chain.

Preferably, the nitrile, oximino, hydrazone or imine groups or the carbonyl groups are bonded directly to the aromatic moiety of the aromatic nitro compound or via a pyrazolyl, pyrimidyl or pyrimidyldione side chain, which can additionally be substituted by oxygen, halogen or by $C_1$–$C_4$alkyl.

The aromatic nitro compounds can be substituted by any further groups desired.

In the context of the present invention, aromatic nitro and amino compounds are to be understood as being those systems that obey the Hückel 4n+2 electron rule, for example aromatic hydrocarbons, such as benzenes, polycyclic hydrocarbons (including partially hydrogenated hydrocarbons, such as 1,2,3,4-tetrahydronaphthalene), biphenyls, the cyclopentadienyl and cycloheptatrienyl anions, anthraquinones, heteroaromatic compounds, such as pyridines, pyrroles, azoles, diazines, triazines, triazoles, furans, thiophenes and oxazoles, and fused aromatic compounds, such as naphthalene, anthracene, indoles, quinolines, isoquinolines, carbazoles, purines, phthalazines, benzotriazoles, benzofurans, cinnolines, quinazoles, acridines and benzothiophenes.

The aromatic nitro compounds can contain one or more nitro groups. They preferably contain one or two nitro groups.

A preferred group of compounds consists of those aromatic nitro compounds that have at least one unsaturated carbon-carbon bond, especially an alkene, alkyne or allene bond.

Those compounds correspond especially to formula I

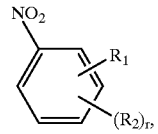

(I)

wherein $R_1$ is a group containing at least one unsaturated carbon-carbon bond, —CN multiple bond or carbonyl group;

r is 1, 2, 3 or 4;

$R_2$ is hydrogen, $C_1$–$C_{12}$alkyl, $C_1$–$C_{12}$haloalkyl, $C_1$–$C_{12}$hydroxyalkyl, $C_1$–$C_6$cyanoalkyl, $C_3$–$C_8$cycloalkyl, $C_6$–$C_{16}$aryl, $C_7$–$C_{16}$aralkyl, $C_3$–$C_6$heterocycloalkyl, $C_3$–$C_{16}$heteroaryl, $C_4$–$C_{16}$heteroaralkyl, halogen, cyano, $COR_3$, $X_1R_4$, —$COR_8$,

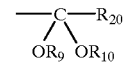

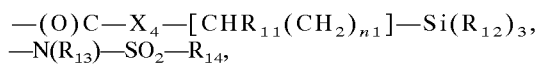
—$N(R_{13})$—$SO_2$—$R_{14}$,

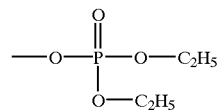

or

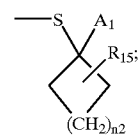

$A_1$ is cyano or —$COR_{16}$;

$R_3$ is halogen, $X_2$—$R_5$, amino, $C_1$–$C_4$alkylamino, di-$C_1$–$C_4$alkylamino, $C_2$–$C_4$haloalkylamino, di-$C_2$–$C_4$haloalkylamino, $C_1$–$C_4$alkoxyalkylamino, di-$C_1$–$C_4$alkoxyalkylamino, $C_2$–$C_4$alkenylamino, diallylamino, —N-pyrrolidino, —N-piperidino, —N-morpholino, —N-thiomorpholino or —N-piperidazino;

$R_4$ is hydrogen, $C_1$–$C_{10}$alkyl, $C_1$–$C_4$alkoxy-$C_1$–$C_4$alkyl, $C_1$–$C_4$alkylthio-$C_1$–$C_4$alkyl, di-$C_1$–$C_4$alkylamino-$C_1$–$C_4$alkyl, halo-$C_1$–$C_8$alkyl, $C_2$–$C_8$alkenyl, halo-$C_2$–$C_8$alkenyl, $C_3$–$C_8$alkynyl, $C_3$–$C_7$cycloalkyl, halo-$C_3$–$C_7$cycloalkyl, $C_1$–$C_8$alkylcarbonyl, aliylcarbonyl, $C_3$–$C_7$cycloalkylcarbonyl; benzoyl that is unsubstituted or substituted on the phenyl ring by up to three identical or different substituents selected from halogen, $C_1$–$C_4$alkyl, halo-$C_1$–$C_4$alkyl, halo-$C_1$–$C_4$alkoxy and $C_1$–$C_4$alkoxy; furanoyl, thienyl; $C_1$–$C_4$alkyl substituted by phenyl, halophenyl, $C_1$–$C_4$alkylphenyl, $C_1$–$C_4$alkoxyphenyl, halo-$C_1$–$C_4$alkylphenyl, halo-$C_1$–$C_4$alkoxyphenyl, $C_1$–$C_6$alkoxycarbonyl, $C_1$–$C_4$alkoxy-$C_1$–$C_8$alkoxycarbonyl, $C_2$–$C_8$alkenyloxycarbonyl, $C_3$–$C_8$alkynyloxycarbonyl, $C_1$–$C_8$alkylthiocarbonyl, $C_2$–$C_8$alkenylthiocarbonyl, $C_3$–$C_8$alkynylthiocarbonyl, carbamoyl, mono-$C_1$–$C_4$alkylamino-carbonyl or by di-$C_1$–$C_4$alkylaminocarbonyl; phenylaminocarbonyl that is unsubstituted or on the phenyl ring is substituted by up to three identical or different substituents selected from halogen, $C_1$–$C_4$alkyl, halo-$C_1$–$C_4$alkyl, halo-$C_1$–$C_4$alkoxy and $C_1$–$C_4$alkoxy or is mono-substituted by cyano; dioxolan-2-yl that is unsubstituted or substituted by one or two $C_1$–$C_4$alkyl groups; dioxan-2-yl that is unsubstituted or substituted by one or two $C_1$–$C_4$alkyl groups; or $C_1$–$C_4$alkyl substituted by cyano, carboxyl or by $C_1$–$C_8$alkylthio-$C_1$–$C_8$alkoxycarbonyl; $R_5$ is hydrogen, $C_1$–$C_{10}$alkyl, $C_1$–$C_4$alkoxy-$C_1$–$C_4$alkyl, halo-$C_1$–$C_8$alkyl, $C_1$–$C_{10}$alkylthio-$C_1$–$C_4$alkyl, di-$C_1$–$C_4$alkylamino-$C_1$–$C_4$alkyl, cyano-$C_1$–$C_8$alkyl, $C_2$–$C_8$alkenyl, halo-$C_2$–$C_8$alkenyl, $C_3$–$C_8$alkynyl, $C_3$–$C_7$cycloalkyl, $C_3$–$C_7$cycloalkyl-$C_1$–$C_4$alkyl, halo-$C_3$–$C_7$cycloalkyl; benzyl that is unsubstituted or substituted on the phenyl ring by up to three identical or different substituents selected from halogen, $C_1$–$C_4$alkyl, halo-$C_1$–$C_4$alkyl, halo-$C_1$–$C_4$alkoxy and $C_1$–$C_4$alkoxy; an alkali metal ion, alkaline earth metal ion or ammonium ion or the group $[CHR_6(CH_2)_{n3}]$—$COOR_7$;

$R_6$ is hydrogen or $C_1$–$C_4$alkyl;

$R_7$ is hydrogen, $C_1$–$C_6$alkyl, $C_2$–$C_8$alkenyl, $C_3$–$C_8$alkynyl, $C_1$–$C_8$alkoxy-$C_2$–$C_8$alkyl, $C_1$–$C_8$alkylthio-thio-$C_1$–$C_8$alkyl or $C_3$–$C_7$cycloalkyl;

$R_8$ and $R_{20}$ are each independently of the other hydrogen, $C_1$–$C_4$alkyl, halo-$C_1$–$C_4$alkyl or $C_1$–$C_4$alkoxy-$C_1$–$C_4$alkyl;

$R_9$ and $R_{10}$ are each independently of the other $C_1$–$C_4$alkyl, $C_2$–$C_4$haloalkyl or $C_2$–$C_8$alkoxy-alkyl, or $R_9$ and $R_{10}$ together form an ethano, propano or cyclohexane-1,2-diyl bridge, those groups being either unsubstituted or mono- or di-substituted by $C_1$–$C_4$alkyl, $C_1$–$C_4$haloalkyl or by $C_1$–$C_4$hydroxyalkyl;

$R_{11}$ is hydrogen, $C_1$–$C_5$alkyl or $C_3$–$C_7$alkenyl;

$R_{12}$ is $C_1$–$C_8$alkyl; $R_{13}$ is hydrogen, $C_1$–$C_5$alkyl, benzyl, halo-$C_1$–$C_4$alkyl, $C_2$–$C_8$alkenyl or $C_3$–$C_8$alkynyl;

$R_{14}$ is $C_1$–$C_6$alkyl, halo-$C_1$–$C_5$alkyl or di-$C_1$–$C_4$alkylamino;

$R_{15}$ is hydrogen, fluorine, chlorine, bromine, $C_1$–$C_4$alkyl or trifluoromethyl;

$R_{16}$ is $X_3$—$R_{17}$, amino, $C_1$–$C_4$alkylamino, di-$C_1$–$C_4$alkylamino, $C_2$–$C_4$haloalkylamino, di-$C_2$–$C_4$haloalkylamino, $C_1$–$C_4$alkoxyalkylamino, di-$C_1$–$C_4$alkoxyalkylamino, $C_2$–$C_4$alkenylamino, diallylamino, —N-pyrrolidino, —N-piperidino, —N-morpholino, —N-thiomorpholino, —N-piperidazino, or a group —O—N=C—(CH$_3$)—CH$_3$, —O—CH$_2$—CH$_2$—O—N=C(CH$_3$)—CH$_3$ or —N(OR$_{24}$)—R$_{22}$;

$R_{17}$ is hydrogen, $C_1$–$C_{10}$alkyl, $C_1$–$C_4$alkoxy-$C_1$–$C_4$alkyl, halo-$C_1$–$C_8$alkyl, $C_1$–$C_{10}$alkylthio-$C_1$–$C_4$alkyl, di-$C_1$–$C_4$alkylamino-$C_1$–$C_4$alkyl, cyano-$C_1$–$C_8$alkyl, $C_2$–$C_8$alkenyl, halo-$C_2$–$C_8$alkenyl, $C_3$–$C_8$alkynyl, $C_3$–$C_7$cycloalkyl, $C_3$–$C_7$cycloalkyl-$C_1$–$C_4$alkyl, halo-$C_3$–$C_7$cycloalkyl; benzyl that is unsubstituted or substituted on the phenyl ring by up to three identical or different substituents selected from halogen, $C_1$–$C_4$alkyl, halo-$C_1$–$C_4$alkyl, halo-$C_1$–$C_4$alkoxy and $C_1$–$C_4$alkoxy; an alkali metal ion, alkaline earth metal ion or ammonium ion, or a group —$[CHR_{25}$—$(CH_2)_m]$—$COOR_{26}$ or $[CHR_{27}$—$(CH_2)_t$—$Si(R_{23})_3]$;

$R_{22}$ is hydrogen or $C_1$–$C_4$alkyl;

$R_{23}$ is $C_1$–$C_4$alkyl, halo-$C_1$–$C_4$alkyl or ClC$_4$alkoxy-$C_1$–$C_4$alkyl;

$R_{24}$ and $R_{25}$ are each independently of the other hydrogen or $C_1$–$C_4$alkyl;

$R_{26}$ is hydrogen, $C_1$–$C_6$alkyl, $C_2$–$C_8$alkenyl, $C_3$–$C_8$alkynyl, $C_1$–$C_8$alkoxy-$C_2$–$C_8$alkyl, $C_1$–$C_8$alkylthio-$C_1$–$C_8$alkyl or $C_3$–$C_7$cycloalkyl;

$R_{27}$ is hydrogen or $C_1$–$C_4$alkyl;

m is 0, 1, 2, 3 or 4;

t is 0, 1, 2, 3 or 4;

n1, n2 and n3 are each independently of the others 0, 1, 2, 3 or 4; and $X_1$, $X_2$, $X_3$ and $X_4$ are each independently of the others oxygen or sulfur.

Preference is given to those compounds of formula I wherein $R_1$ is a group containing an unsaturated carbon-carbon bond.

In the compounds of formula I r is preferably 1 or 2. Special mention should also be made of those compounds of formula I wherein the unsaturated carbon-carbon bond of the substituent $R_1$ is part of an ester group.

A further preferred sub-group of compounds of formula I consists of those wherein $R_2$ is hydrogen, halogen, $C_1$–$C_6$alkyl, $C_1$–$C_6$alkoxy, $C_1$–$C_6$haloalkoxy or cyano, with $R_2$ especially being hydrogen, halogen, methyl, difluoromethoxy, trifluoromethoxy or cyano.

The process according to the invention is especially suitable for the conversion into the corresponding amino compounds of aromatic nitro compounds of formula Ia

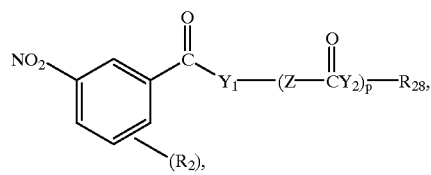

(Ia)

wherein $R_2$ and r are as defined for formula I and $R_{28}$ is $C_2$–$C_6$alkenyl, $C_3$–$C_6$alkynyl, $C_3$–$C_8$cycloalkenyl or $C_6$–$C_8$bicycloalkenyl;

$Y_1$ is oxygen, —NH—, a group

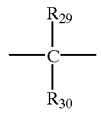

or a group

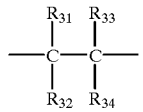

$R_{29}$ and $R_{30}$ are each independently of the other hydrogen or $C_1$–$C_4$alkyl; or $R_{29}$ and $R_{30}$, together with the carbon atom to which they are bonded, form a 3- to 7-membered ring which may contain one or two oxygen atoms or a group $NR_{35}$, wherein $R_{35}$ is hydrogen, $C_1$–$C_4$alkyl or $C_1$–$C_4$alkylcarbonyl;

$R_{31}$, $R_{32}$, $R_{33}$ and $R_{34}$ are each independently of the others hydrogen or $C_1$–$C_4$alkyl, or $R_{31}$ and $R_{32}$ or $R_{33}$ and $R_{34}$, together with the carbon atom to which they are bonded, form a 3- to 7-membered ring which may contain one or two oxygen atoms or a group $NR_{36}$, wherein $R_{36}$ is hydrogen or $C_1$–$C_4$alkyl;

$Y_2$ is oxygen, —NH—, a group

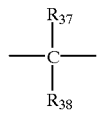

or a group

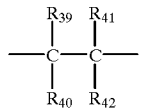

$R_{37}$ and $R_{38}$ are each independently of the other hydrogen or $C_1$–$C_4$alkyl; or $R_{37}$ and $R_{38}$, together with the carbon atom to which they are bonded, form a 3- to 7-membered ring which may contain one or two oxygen atoms or a group $NR_{35}$, wherein $R_{35}$ is hydrogen, $C_1$–$C_4$alkyl or $C_1$–$C_4$alkylcarbonyl;

$R_{39}$, $R_{40}$, $R_{41}$ and $R_{42}$ are each independently of the others hydrogen or $C_1$–$C_4$alkyl, or $R_{39}$ and $R_{40}$ or $R_{41}$ and $R_{42}$, together with the carbon atom to which they are bonded, form a 3- to 7-membered ring which may contain one or two oxygen atoms or a group $NR_{43}$, wherein $R_{43}$ is hydrogen or $C_1$–$C_4$alkyl;

Z is the group

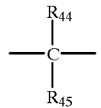

or the group

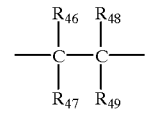

$R_{44}$, $R_{45}$, $R_{46}$, $R_{47}$, $R_{48}$ and $R_{49}$ are each independently of the others hydrogen or methyl; and p is 0 or 1, and, in the compound of formula Ia, preferably r is 1 or 2 and $R_2$ is hydrogen, halogen, $C_1$–$C_6$alkyl, $C_1$–$C_6$alkoxy, $C_1$–$C_6$haloalkoxy or cyano.

Of that group of compounds of formula Ia special mention should be made of those wherein $R_2$ is hydrogen, halogen, methyl, difluoromethoxy, trifluoromethoxy or cyano, and especially p is 1, and $Y_1$ and $Y_2$ are oxygen. In especially preferred compounds of formula Ia from that group, Z is a group

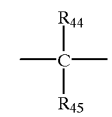

wherein $R_{44}$ and $R_{45}$ are preferably methyl.

A further sub-group of compounds of formula I corresponds to formula Ib

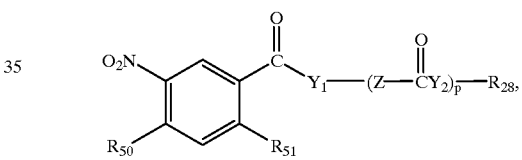

(Ib)

wherein $Y_1$, $Y_2$, Z, p and $R_{28}$ are as defined for formula Ia and $R_{50}$ is hydrogen or halogen; and $R_{51}$ is hydrogen, halogen, methyl, difluoromethoxy, trifluoromethoxy or cyano, and preferably $R_{50}$ is hydrogen, $R_{51}$ is chlorine and $R_{28}$ is allyl.

If the compounds of formula I have a centre of asymmetry, the compounds may occur in optically isomeric forms. Some compounds of formula I may be present in tautomeric forms (e.g. keto-enol tautomerism). If an aliphatic C=C double bond is present, geometric isomerism may also occur (E form or Z form). Furthermore, exo-endo configurations are also possible. Formula I includes all possible stereoisomers, which are present in the form of enantiomers, tautomers, diastereoisomers, E/Z isomers or mixtures thereof.

In the above definitions, halogen is to be understood as being fluorine, chlorine, bromine or iodine, preferably fluorine, chlorine or bromine.

Alkyl is methyl, ethyl, isopropyl, n-propyl, n-butyl, isobutyl, sec-butyl, tert-butyl or the various isomers of pentyl, hexyl, heptyl, octyl, nonyl, decyl, undecyl or dodecyl radicals.

Haloalkyl is, for example, fluoromethyl, difluoromethyl, trifluoromethyl, chloro methyl, dichloromethyl, trichloromethyl, 2,2,2-trifluoroethyl, 2-fluoroethyl, 2-chloroethyl or 2,2,2-trichloroethyl, preferably trichloromethyl, difluorochioromethyl, trifluoromethyl or dichloro-fluoromethyl.

Alkoxy is, for example, methoxy, ethoxy, propyloxy, iso-propyloxy, n-butyloxy, iso-butyloxy, sec-butyloxy or tert-butyloxy, preferably methoxy or ethoxy.

Haloalkoxy is, for example, fluoromethoxy, difluoromethoxy, trifluoromethoxy, 2,2,2-trifluoro-ethoxy, 1,1,2,2-tetrafluoroethoxy, 2-fluoroethoxy, 2-chloroethoxy or 2,2,2-trichloroethoxy, preferably difluoromethoxy, 2-chloroethoxy or trifluoromethoxy.

Alkylthio is, for example, methylthio, ethylthio, propylthio, isopropylthio, n-butylthio, iso-butylthio, sec-butylthio, tert-butylthio or the isomers of pentylthio, preferably methyl thio or ethylthio.

Alkenyl is to be understood as being straight-chained or branched alkenyl, for example vinyl, allyl, methallyl, 1-methylvinyl, but-2-en-1-yl, pentenyl, 2-hexenyl or 3-heptenyl.

Preference is given to alkenyl radicals having a chain length of 2 or 3 carbon atoms. The olefinic double bond may be mono-, di-, tri- or tetra-substituted.

The alkynyl radicals appearing in the definitions of the substituents may be straight-chained or branched, such as, for example, propargyl, 3-butynyl, 1-methylpropargyl, 1-pentynyl or 2-hexynyl. The alkyne function may be mono- or di-substituted.

Cycloalkyl is, for example, cyclopropyl, dimethylcyclopropyl, cyclobutyl, cyclo pentyl, methylcyclopentyl, cyclohexyl or cycloheptyl, but preferably cyclo propyl, cyclopentyl or cyclohexyl.

Alkoxycarbonyl is, for example, methoxycarbonyl, ethoxycarbonyl, n-propyloxycarbonyl, isopropyloxycarbonyl or n-butyloxycarbonyl, preferably methoxycarbonyl or ethoxy carbonyl.

Alkoxyalkyl is, for example, methoxymethyl, ethoxymethyl, propyloxymethyl, methoxyethyl, ethoxyethyl, propyloxyethyl, methoxypropyl, ethoxypropyl or propyloxypropyl.

Alkylthioalkyl is, for example, methylthiomethyl, ethylthiomethyl, methylthioethyl, ethylthioethyl or isopropylthioethyl.

Alkylaminoalkyl is, for example, methylaminoethyl, dimethylaminoethyl, ethylaminoethyl or diethylaminoethyl.

Cyanoalkyl is, for example, cyanomethyl, cyanoethyl or cyanopropyl.

Halocycloalkyl is, for example, 2,2-dichlorocyclopropyl or pentachlorocyclohexyl.

Alkylsulfonyl is, for example, methylsulfonyl, ethylsulfonyl, propylsulfonyl or butylsulfonyl. Methyl- and ethyl-sulfonyl are preferred.

Phenyl, including as part of a substituent such as phenoxy, phenylthio, phenoxy carbonyl, phenylaminocarbonyl, benzyl or benzoyl, may generally be present in unsubstituted form or substituted by further substituents. The substituents may then be in the ortho, meta and/or para positions. The ortho and para positions relative to the ring linkage site are preferred substituent positions. Halogen atoms are preferred substituents.

Aralkyl is, for example, benzyl, phenethyl, 3-phenylpropyl, α-methylbenzyl, phenbutyl or α,α-dimethylbenzyl.

Aryl is, for example, phenyl, 1,2,3,4-tetrahydronaphthalene, indene, naphthalene, azulene or anthracene.

Heteroaryl is, for example, pyrrole, furan, thiophene, oxazole, thiazole, pyridine, pyrazine, pyrimidine, pyridazine, indole, purine, quinoline or isoquinoline.

Heterocloalkyl is, for example, oxirane, oxetane, azetidine, azirine, 1,2-oxathiolane, pyrazoline, pyrrolidine, piperidine, piperazine, morpholine, dioxolane, tetrahydropyran, tetrahydrofuran or tetrahydrothiophene.

Specific, especially preferred individual compounds of formula Ic

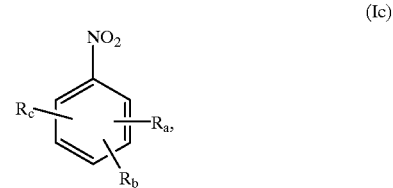

(Ic)

which can be hydrogenated to compounds of formula Id

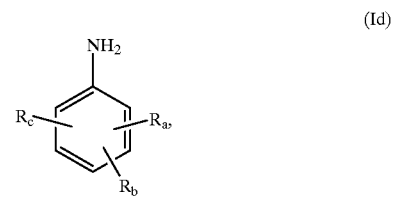

(Id)

are listed in

Table 1. The positions of the substituents are with respect to the nitro group in the 1-position.

TABLE 1

| Comp. No. | $R_a$ | $R_b$ | $R_c$ |
| --- | --- | --- | --- |
| 101 | 3-COO—C(CH$_3$)$_2$COO—CH$_2$—CH=CH$_2$ | 4-Cl | H; |
| 102 | 3-OCH$_3$—C≡CH | 4-O—CH$_2$—C≡CH | 5-Cl; |
| 103 | 4-O—CH$_2$—C≡CH | 3-CONH—C$_1$-C$_{12}$alkyl | H; |
| 104 | 3-SCH$_2$CH=CH—CH=CCl$_2$ | 6-NH$_2$ | H; |
| 105 | 3-NO$_2$ | —COOC$_2$H$_4$OCOC(CH$_3$)$_2$=CH$_2$ | H; |
| 106 | 3-OCH$_2$CH=CH$_2$ | H | H; |
| 107 | 3-NO$_2$ | 4-C≡CH | H; |
| 108 | 3-CH=CH$_2$ | H | H; |
| 109 | 3-C≡C—C(CH$_3$)$_3$ | H | H. |

The invention relates also to the use of a phosphorus-modified noble metal catalyst for the catalytic hydrogenation of substituted aromatic nitro compounds containing at least one carbon-carbon, carbon-nitrogen or carbon-oxygen multiple bond on the aromatic moiety or in a side chain.

The Examples that follow illustrate the invention.

EXAMPLE A1

Impregnation of Active Carbon with Ammonium Vanadate 300 mg of ammonium vanadate are placed in a vessel having a stirrer together with 600 ml of deionised water. Then 20 g of active carbon are added thereto and the mixture is stirred for 30 minutes. The impregnated active carbon is then filtered off and washed with 600 ml of deionised water in portions. Finally, the vanadium-containing carbon is dried to constant weight in a vacuum drying cabinet at 60° C. 18.8 g of modified carbon having a vanadium content of 13.6 mg/g are obtained.

EXAMPLES B

Hydrogenations

EXAMPLE B 1

Preparation of 2-(2-chloro-5amino-benzoyloxy)-2-methyl-propionic Acid Allyl Ester 0.9 g of vanadium-containing active carbon prepared according to Example A1 is added to a solution of 16.1 g of 2-(2-chloro-5-nitrobenzoyloxy)-2-methyl-propionic acid allyl ester and 100 mg of toluene in an autoclave having a stirrer. 82 mg of platinum-carbon catalyst together with 50 mg of hypophosphorous acid and 2 ml of deionised water are placed in a seperate glass vessel, and the mixture is stirred for 10 minutes. The catalyst suspension is then transferred to the autoclave, rinsing the glass vessel with 4 ml of deionised water, and hydrogenated for 2 hours at a temperature of 100° C. and a hydrogen pressure of 20 bar. After cooling and rendering the autoclave inert using nitrogen, the catalyst is filtered off and washed with 20 ml of toluene. After working up by distillation, 14 g of 2-(2-chloro- 5-amino-benzoyloxy)-2-methyl-propionic acid allyl ester having a content of 98.9% according to HPLC are obtained (yield 94.8% of theory).

$^1$H-NMR (CDCl$_3$, 250 MHz) 1.62 ppm (s, 6H); 3.65 ppm (s, 2H); 4.6 ppm (d, 2H); 5.2 ppm (q, 2H); 5.85 ppm (m, 1H); 6.65 ppm (m, 1H); 7.0 ppm (m, 1H); 7.1 ppm (m, 1H). Examples B2–B5. The procedure is as described in Example B1 and the amino compounds mentioned in Table 2 are obtained from the corresponding nitro compounds.

TABLE 2

| No. | Product | Yield | $^1$H-NMR |
|---|---|---|---|
| 2 | [structure: 3-aminophenyl-CH=CH-COOH] | 95% | 4.5–6 ppm (broad, 3H); 6.32 ppm (d, 1H); 6.60 ppm (m, 1H); 6.80 ppm (m, 2H); 7.05 ppm (m, 1H); 7.42 ppm (d, 1H) |
| 3 | [structure: 3-aminophenyl-CH=CH$_2$] | 95% | 3.66 (s, 2H); 5.22 (d, 1H); 5.70 (d, 1H); 6.65 (m, 4H); 7.13 (m, 1H) |
| 4 | [structure: 3-aminobenzoic acid propargyl ester] | 99% | 2.54 ppm (s, 1H); 3.75 ppm (s, 2H); 4.93 ppm (s, 2H); 6.90 ppm (m, 1H); 7.23 ppm (m, 1H); 7.45 ppm (m, 2H) |

TABLE 2-continued

| No. | Product | Yield | ¹H-NMR |
|---|---|---|---|
| 5 | 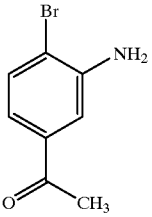 | 93% | 2.5 ppm (s, 3H); 4.17 ppm (s, 2H); 7.1 ppm (m, 1H); 7.28 ppm (m, 1H); 7.43 ppm (m, 1H) |

EXAMPLE B6

Preparation of 2-(2-chloro-5amino-benzoyloxy)-2-methyl-propionic Acid Allyl Ester 5.9 kg of 5% Pt/C catalyst 5% (H$_2$O content: 62.8%) are placed in a 60-liter steel vessel together with 12 liters of water, and 470 g of 50% H$_3$PO$_2$ solution (≡5% phosphorus based on the catalyst) are added. The catalyst slurry is stirred for 10 minutes at room temperature, then 360 g of vanadylacetylacetonate VO(acac)$_2$ as is (0.2 mol %) are added and the mixture is stirred for a further 5 minutes. 550 kg of a solution of 2-(chloro-5-nitro-benzoyl-oxy)-2-methyl-propionic acid allyl ester (content: 40%, 0.67 kmol) in toluene are placed in an autoclave having a stirrer and the catalyst suspension is added, rinsing the steel vessel with 15 kg of water. Hydrogenation is then carried out for 2 hours at a temperature of 100° C. and a hydrogen pressure of 5 bar. After cooling and rendering the autoclave inert using nitrogen, the catalyst is filtered off at 50° C. and washed with 50 kg of toluene. After working up by distillation, 196 kg of 2-(chloro-5-amino-benzoyloxy)-2-methyl-propionic acid allyl ester (yield 98% of theory) are obtained. The overhydrogenated propyl ester content is <0.05%.

¹H-NMR (CDCl$_3$, 250 MHz) 1.62 ppm (s, 6H); 3.65 ppm (s, 2H); 4.6 ppm (d, 2H); 5.2 ppm (q, 2H); 5.85 ppm (m, 1H); 6.65 ppm (m, 1H); 7.0 ppm (m, 1 H); 7.1 ppm (m, 1H).

What is claimed is:

1. A process for the preparation of substituted aromatic amino compounds containing at least one carbon-carbon, carbon-nitrogen or carbon-oxygen multiple bond on the aromatic moiety or in a side chain, by means of catalytic hydrogenation of corresponding substituted aromatic nitro compounds in the presence of a modified noble metal catalyst, wherein rhodium, ruthenium, iridium, platinum or palladium modified with an inorganic or organic phosphorus compound having an oxidation state of less than 5 is used as the noble metal catalyst.

2. A process according to claim 1, wherein platinum or palladium is used as the noble metal catalyst.

3. A process according to claim 1, wherein platinum is used as the noble metal catalyst.

4. A process according to claim 1, wherein the noble metal catalyst is used in an amount of from 0.1 to 10% by weight, based on the aromatic nitro compound used.

5. A process according to claim 1, wherein the noble metal catalyst is used in an amount of from 0.5 to 2% by weight, based on the aromatic nitro compound used.

6. A process according to claim 3, wherein the noble metal catalyst used in the modification is applied in metallic or oxidised form to a carrier.

7. A process according to claim 6, wherein the carrier is active carbon, silicon dioxide in the form of silicic acid, silica gel, aluminium oxide, calcium carbonate, calcium phosphate, calcium sulfate, barium sulfate, titanium oxide, magnesium oxide, iron oxide, lead oxide, lead sulfate or lead carbonate.

8. A process according to claim 7, wherein the carrier is active carbon, aluminium oxide or silicon dioxide.

9. A process according to claim 6, wherein the noble metal catalyst contains from 1 to 10% by weight platinum.

10. A process according to claim 1, wherein the modifying phosphorus compound is selected from the group: phosphines P(R$_a$)$_{3-n}$(H)$_n$, phosphinous acids HO—P(H)$_m$(R$_a$)$_{2-m}$, phosphine oxides O=P(R$_a$)$_{3-n}$(H)$_n$, hypophosphonous acids

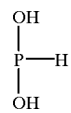

and

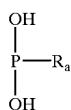

hypophosphorous acids O=P(OH)(H)$_m$(R$_a$)$_{2-m}$ and phosphorous acids O=P(OH)$_2$H and O=P(OH)$_2$R$_a$, wherein R$_a$ is linear or branched C$_1$–C$_{12}$alkyl, C$_6$–C$_{16}$aryl or C$_4$–C$_{16}$heteroaryl, m is 0, 1 or 2 and n is 0, 1, 2 or 3.

11. A process according to claim 1, wherein diphenylphosphine, triphenylphosphine, phosphinous acid or a salt, amide or ester thereof, diphenylphosphinic acid, diphenyl phosphite, a phosphine oxide, phosphorous acid or a salt or ester thereof, or hypophos phorous acid or a salt or ester thereof is used as the modifying phosphorus compound.

12. A process according to claim 11, wherein phosphorous acid or a salt or ester thereof or hypophosphorous acid or a salt or ester thereof is used as the modifying phosphorus compound.

13. A process according to claim 1, wherein the modification of the noble metal catalyst with the phosphorus compound is carried out in situ before the hydrogenation.

14. A process according to claim 1, wherein the ratio of noble metal catalyst to the modifying phosphorus compound is from 1:0.1 to 1:1000 parts by weight.

15. A process according to claim 1, wherein the ratio of noble metal catalyst to the modifying phosphorus compound is from 1:5 to 1:200 parts by weight.

16. A process according to claim 1, wherein a transition metal ion from the group $Fe^{2+}$, $Fe^{3+}$, $Ru^{3+}$, $Mn^{2+}$, $Mn^{3+}$, $Co^{2+}$, $Co^{3+}$ or a vanadium compound in which the vanadium has the oxidation state 0, II, III, IV or V is added as co-catalyst.

17. A process according to claim 16, wherein a vanadium compound in which the vanadium has the oxidation state 0, II, III, IV or V is added as co-catalyst.

18. A process according to claim 17, wherein the vanadium compound is dissolved or dispersed in catalytic amounts in the reaction medium.

19. A process according to claim 17, wherein the vanadium compound is first of all applied to a suitable carrier material and dispersed in that form in the reaction medium.

20. A process according to claim 17, wherein the vanadium compound is selected from the group: vanadium(III) acetylacetonate, vanadium(IV) oxyacetylacetonate, $V_2O_5$, $VOCl_3$, $VCl_6^-$, $[(VO(SCN)_4]^{2-}$, $VOSO_4$, $NH_4VO_3$, $LiVO_3$, $NaVO_3$, $KVO_3$, $VCl_3$, $VCl_2$ and the corresponding halides with F or Br.

21. A process according to claim 20, wherein an ammonium, lithium, sodium or potassium vanadate or a hydrate of those vanadates is used.

22. A process according to claim 20, wherein vanadium (III) acetyl acetonate or vanadium(IV) oxyacetylacetonate is used.

23. A process according to claim 1, wherein the vanadium compound is used in an amount of from 1 to 2000 ppm, based on the aromatic nitro compound to be hydrogenated.

24. A process according to claim 23, wherein the vanadium compound is used in an amount of from 5 to 1000 ppm, based on the aromatic nitro compound to be hydrogenated.

25. A process according to claim 1, wherein the ratio by weight of vanadium compound to noble metal catalyst is from 1:1 to 1:10000.

26. A process according to claim 25, wherein the ratio by weight of vanadium compound to noble metal catalyst is from 1:50 to 1:750.

27. A process according to claim 1, wherein the process is carried out at a pressure of from 1 to 100 bar.

28. A process according to claim 27, wherein the process is carried out at a pressure of from 1 to 40 bar.

29. A process according to claim 1, wherein the temperature is from 0 to +160° C.

30. A process according to claim 29, wherein the temperature is from +20° to +100° C.

31. A process according to claim 1, wherein, if the compound to be hydrogenated is liquid at the reaction temperature, the hydrogenation is carried out without a solvent.

32. A process according to claim 1, wherein tetrahydrofuran, toluene or xylene is used as solvent.

33. A process according to claim 1, wherein the aromatic nitro compound has at least one unsaturated carbon-carbon bond.

34. A process according to claim 1, wherein the compound corresponds to formula I

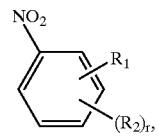

wherein
$R_1$ is a group containing at least one unsaturated carbon-carbon bond, —CN multiple bond or carbonyl group;
r is 1, 2, 3 or 4;
$R_2$ is hydrogen, $C_1$–$C_{12}$alkyl, $C_1$–$C_{12}$haloalkyl, $C_1$–$C_{12}$hydroxyalkyl, $C_1$–$C_6$cyanoalkyl, $C_3$–$C_8$cycloalkyl, $C_6$–$C_{16}$aryl, $C_7$–$C_{16}$aralkyl, $C_3$–$C_6$heterocycloalkyl, $C_3$–$C_{16}$heteroaryl, $C_4$–$C_{16}$heteroaralkyl, halogen, cyano, $COR_3$, $X_1R_4$, —$COR_8$,

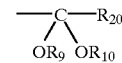

—(O)C—$X_4$—[$CHR_{11}(CH_2)_{n1}$]—$Si(R_{12})_3$, —$N(R_{13})$—$SO_2$—$R_{14}$,

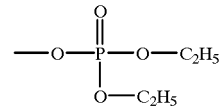

or

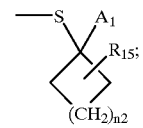

$A_1$ is cyano or —$COR_{16}$;
$R_3$ is halogen, $X_2$—$R_5$, amino, $C_1$–$C_4$alkylamino, di-$C_1$–$C_4$alkylamino, $C_2$–$C_4$haloalkylamino, di-$C_2$–$C_4$haloalkylamino, $C_1$–$C_4$alkoxyalkylamino, di-$C_1$–$C_4$alkoxyalkylamino, $C_2$–$C_4$alkenylamino, diallylamino, —N-pyrrolidino, —N-piperidino, —N-morpholino, —N-thiomorpholino or —N-piperidazino;
$R_4$ is hydrogen, $C_1$–$C_{10}$alkyl, $C_1$–$C_4$alkoxy-$C_1$–$C_4$alkyl, $C_1$–$C_4$alkylthio-$C_1$–$C_4$alkyl, di-$C_1$–$C_4$alkylamino-$C_1$–$C_4$alkyl, halo-$C_1$–$C_8$alkyl, $C_2$–$C_8$alkenyl, halo-$C_2$–$C_8$alkenyl, $C_3$–$C_8$alkynyl, $C_3$–$C_7$cycloalkyl, halo-$C_3$–$C_7$cycloalkyl, $C_1$–$C_8$alkylcarbonyl, allylcarbonyl, $C_3$–$C_7$cycloalkylcarbonyl; benzoyl that is unsubstituted or substituted on the phenyl ring by up to three identical or different substituents selected from halogen, $C_1$–$C_4$alkyl, halo-$C_1$–$C_4$alkyl, halo-$C_1$–$C_4$alkoxy and $C_1$–$C_4$alkoxy; furanoyl, thienyl; $C_1$–$C_4$alkyl substituted by phenyl, halophenyl, $C_1$–$C_4$alkylphenyl, $C_1$–$C_4$alkoxyphenyl, halo-$C_1$–$C_4$alkylphenyl, halo-$C_1$–$C_4$alkoxyphenyl, $C_1$–$C_6$alkoxycarbonyl, $C_1$–$C_4$alkoxy-$C_1$–$C_8$alkoxycarbonyl, $C_2$–$C_8$alkenyloxycarbonyl, $C_3$–$C_8$alkynyloxycarbonyl, $C_1$–$C_8$alkylthiocarbonyl, $C_2$–$C_8$alkenylthiocarbonyl, $C_3$–$C_8$alkynylthiocarbonyl, carbamoyl, mono-$C_1$–$C_4$alkylamino-carbonyl or by di-$C_1$–$C_4$alkylaminocarbonyl; phenylaminocarbonyl that is unsubstituted or on the phenyl ring is substituted by up to three identical or different substituents selected from halogen, $C_1$–$C_4$alkyl, halo-$C_1$–$C_4$alkyl, halo-$C_1$–$C_4$alkoxy and $C_1$–$C_4$alkoxy or is mono-substituted by cyano; dioxolan-2-yl that is unsubstituted or substituted by one or two $C_1$–$C_4$alkyl groups; dioxan-2-yl that is unsubstituted or substituted by one or two $C_1$–$C_4$alkyl groups; or $C_1$–$C_4$alkyl substituted by cyano, carboxyl or by $C_1$–$C_8$alkylthio-$C_1$–$C_8$alkoxycarbonyl;

$R_5$ is hydrogen, $C_1$–$C_{10}$alkyl, $C_1$–$C_4$alkoxy-$C_1$–$C_4$alkyl, halo-$C_1$–$C_8$alkyl, $C_1$–$C_{10}$alkylthio-$C_1$–$C_4$alkyl, di-$C_1$–$C_4$alkylamino-$C_1$–$C_4$alkyl, cyano-$C_1$–$C_8$alkyl, $C_2$–$C_8$alkenyl, halo-$C_2$–$C_8$alkenyl, $C_3$–$C_8$alkynyl, $C_3$–$C_7$cycloalkyl, $C_3$–$C_7$cycloalkyl-$C_1$–$C_4$alkyl, halo-$C_3$–$C_7$cycloalkyl; benzyl that is unsubstituted or substituted on the phenyl ring by up to three identical or different substituents selected from halogen, $C_1$–$C_4$alkyl, halo-$C_1$–$C_4$alkyl, halo-$C_1$–$C_4$alkoxy and $C_1$–$C_4$alkoxy; an alkali metal ion, alkaline earth metal ion or ammonium ion or the group $[CHR_6(CH_2)_{n3}]$—$COOR_7$;

$R_6$ is hydrogen or $C_1$–$C_4$alkyl;

$R_7$ is hydrogen, $C_1$–$C_6$alkyl, $C_2$–$C_8$alkenyl, $C_3$–$C_8$alkynyl, $C_1$–$C_8$alkoxy-$C_2$–$C_8$alkyl, $C_1$–$C_8$alkylthio-$C_1$–$C_8$alkyl or $C_3$–$C_7$cycloalkyl;

$R_8$ and $R_{20}$ are each independently of the other hydrogen, $C_1$–$C_4$alkyl, halo-$C_1$–$C_4$alkyl or $C_1$–$C_4$alkoxy-$C_1$–$C_4$alkyl;

$R_9$ and $R_{10}$ are each independently of the other $C_1$–$C_4$alkyl, $C_2$–$C_4$haloalkyl or $C_2$–$C_8$alkoxy-alkyl, or $R_9$ and $R_{10}$ together form an ethano, propano or cyclohexane-1,2-diyl bridge, those groups being either unsubstituted or mono- or di-substituted by $C_1$–$C_4$alkyl, $C_1$–$C_4$haloalkyl or by $C_1$–$C_4$hydroxyalkyl;

$R_{11}$ is hydrogen, $C_1$–$C_5$alkyl or $C_3$–$C_7$alkenyl;

$R_{12}$ is $C_1$–$C_8$alkyl;

$R_{13}$ is hydrogen, $C_1$–$C_5$alkyl, benzyl, halo-$C_1$–$C_4$alkyl, $C_2$–$C_8$alkenyl or $C_3$–$C_8$alkynyl;

$R_{14}$ is $C_1$–$C_6$alkyl, halo-$C_1$–$C_5$alkyl or di-$C_1$–$C_4$alkylamino;

$R_{15}$ is hydrogen, fluorine, chlorine, bromine, $C_1$–$C_4$alkyl or trifluoromethyl;

$R_{16}$ is $X_3$—$R_{17}$, amino, $C_1$–$C_4$alkylamino, di-$C_1$–$C_4$alkylamino, $C_2$–$C_4$haloalkylamino, di-$C_2$–$C_4$haloalkylamino, $C_1$–$C_4$alkoxyalkylamino, di-$C_1$–$C_4$alkoxyalkylamino, $C_2$–$C_4$alkenylamino, diallylamino, —N-pyrrolidino, —N-piperidino, —N-morpholino, —N-thiomorpholino, —N-piperidazino, or a group —O—N=C—(CH$_3$)—CH$_3$, —O—CH$_2$—CH$_2$—O—N=C(CH$_3$)—CH$_3$ or —N(OR$_{24}$)—R$_{22}$;

$R_{17}$ is hydrogen, $C_1$–$C_{10}$alkyl, $C_1$–$C_4$alkoxy-$C_1$–$C_4$alkyl, halo-$C_1$–$C_8$alkyl, $C_1$–$C_{10}$alkylthio-$C_1$–$C_4$alkyl, di-$C_1$–$C_4$alkylamino-$C_1$–$C_4$alkyl, cyano-$C_1$–$C_8$alkyl, $C_2$–$C_8$alkenyl, halo-$C_2$–$C_8$alkenyl, $C_3$–$C_8$alkynyl, $C_3$–$C_7$cycloalkyl, $C_3$–$C_7$cyloalkyl-$C_1$–$C_4$alkyl, halo-$C_3$–$C_7$cycloalkyl; benzyl that is unsubstituted or substituted on the phenyl ring by up to three identical or different substituents selected from halogen, $C_1$–$C_4$alkyl, halo-$C_1$–$C_4$alkyl, halo-$C_1$–$C_4$alkoxy and $C_1$–$C_4$alkoxy; an alkali metal ion, alkaline earth metal ion or ammonium ion, or a group —$[CHR_{25}$—$(CH_2)_m]$—$COOR_{26}$ or $[CHR_{27}$—$(CH_2)_t$—$Si(R_{23})_3]$;

$R_{22}$ is hydrogen or $C_1$–$C_4$alkyl;

$R_{23}$ is $C_1$–$C_4$alkyl, halo-$C_1$–$C_4$alkyl or $C_1$–$C_4$alkoxy-$C_1$–$C_4$alkyl;

$R_{24}$ and $R_{25}$ are each independently of the other hydrogen or $C_1$–$C_4$alkyl;

$R_{26}$ is hydrogen, $C_1$–$C_6$alkyl, $C_2$–$C_8$alkenyl, $C_3$–$C_8$alkynyl, $C_1$–$C_8$alkoxy-$C_2$–$C_8$alkyl, $C_1$–$C_8$alkylthio-$C_1$–$C_8$alkyl or $C_3$–$C_7$cycloalkyl;

$R_{27}$ is hydrogen or $C_1$–$C_4$alkyl;

m is 0, 1, 2, 3 or 4;

t is 0, 1, 2, 3 or 4;

n1, n2 and n3 are each independently of the others 0, 1, 2, 3 or 4; and $X_1$, $X_2$, $X_3$ and $X_4$ are each independently of the others oxygen or sulfur.

35. A process according to claim 34 wherein $R_1$ in the compound of formula I is a group containing an unsaturated carbon-carbon bond.

36. A process according to claim 34 wherein r in the compound of formula I is 1 or 2.

37. A process according to claim 34 wherein $R_2$ in the compound of formula I is hydrogen, halogen, $C_1$–$C_6$alkyl, $C_1$–$C_6$alkoxy, $C_1$–$C_6$haloalkoxy or cyano.

38. A process according to claim 34 wherein an aromatic nitro compound of formula Ia

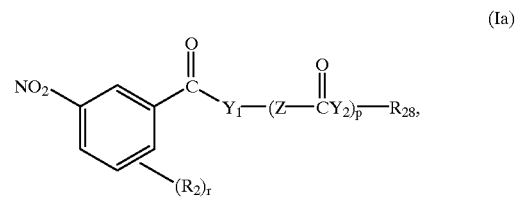

(Ia)

wherein $R_2$ and r are as defined in claim 34 and $R_{28}$ is $C_2$–$C_6$alkenyl, $C_3$–$C_6$alkynyl, $C_3$–$C_8$cycloalkenyl or $C_6$–$C_8$bicycloalkenyl;

$Y_1$ is oxygen, —NH—, a group

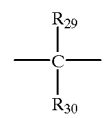

or a group

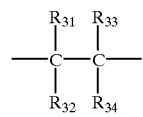

$R_{29}$ and $R_{30}$ are each independently of the other hydrogen or $C_1$–$C_4$alkyl; or $R_{29}$ and $R_{30}$, together with the carbon atom to which they are bonded, form a 3- to 7-membered ring which may contain one or two oxygen atoms or a group $NR_{35}$, wherein $R_{35}$ is hydrogen, $C_1$–$C_4$alkyl or $C_1$–$C_4$alkylcarbonyl;

$R_{31}$, $R_{32}$, $R_{33}$ and $R_{34}$ are each independently of the others hydrogen or $C_1$–$C_4$alkyl; or $R_{31}$ and $R_{32}$ or $R_{33}$ and $R_{34}$, together with the carbon atom to which they are bonded, form a 3- to 7-membered ring which may contain one or two oxygen atoms or a group $NR_{36}$, wherein $R_{36}$ is hydrogen or $C_1$–$C_4$alkyl;

$Y_2$ is oxygen, —NH—, a group

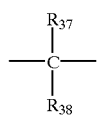

or a group

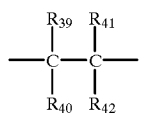

$R_{37}$ and $R_{38}$ are each independently of the other hydrogen or $C_1$–$C_4$alkyl; or $R_{37}$ and $R_{38}$, together with the carbon atom to which they are bonded, form a 3- to 7-membered ring which may contain one or two oxygen atoms or a group $NR_{35}$, wherein $R_{35}$ is hydrogen, $C_1$–$C_4$alkyl or $C_1$–$C_4$alkylcarbonyl;

$R_{39}$, $R_{40}$, $R_{41}$ and $R_{42}$ are each independently of the others hydrogen or $C_1$–$C_4$alkyl, or $R_{39}$ and $R_{40}$ or $R_{41}$ and $R_{42}$, together with the carbon atom to which they are bonded, form a 3- to 7-membered ring which may contain one or two oxygen atoms or a group $NR_{43}$, wherein $R_{43}$ is hydrogen or $C_1$–$C_4$alkyl;

Z is a group

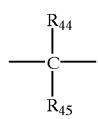

or a group

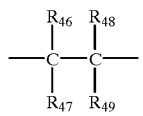

$R_{44}$, $R_{45}$, $R_{46}$, $R_{47}$, $R_{48}$ and $R_{49}$ are each independently of the others hydrogen or methyl; and p is 0 or 1, is hydrogenated to the corresponding amino compound, and, in the compound of formula Ia, preferably r is 1 or 2 and $R_2$ is hydrogen, halogen, $C_1$–$C_6$alkyl, $C_1$–$C_6$alkoxy, $C_1$–$C_6$haloalkoxy or cyano.

39. A process according to claim 37 wherein, in the compound of formula Ia, $R_2$ is hydrogen, halogen, methyl, difluoromethoxy, trifluoromethoxy or cyano, and especially p is 1, and $Y_1$ and $Y_2$ are oxygen.

40. A process according to claim 37 wherein, in the compound of formula Ia, Z is a group

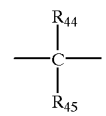

wherein $R_{44}$ and $R_{45}$ are methyl.

41. A process according to claim 34 wherein the compound corresponds to formula Ib (Ib)

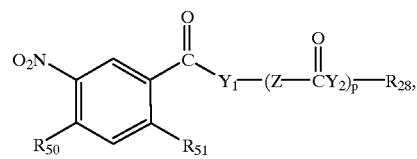

wherein $R_{28}$ is $C_2$–$C_6$alkanyl, $C_3$–$C_6$alknyl, $C_3$–$C_8$cycloalkenyl or $C_6$–$C_8$bicycloalkenyl;

$Y_1$ is oxygen, —NH—, a group

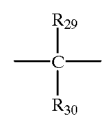

or a group

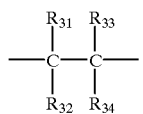

$R_{29}$ and $R_{30}$ are ach independently of the other hydrogen or $C_1$–$C_4$alkyl; or $R_{29}$ and $R_{30}$, together with the carbon atom to which they are bonded, form a 3- to 7-membered ring which may contain one or two oxygen atoms or a group $NR_{35}$, wherein $R_{35}$ is hydrogen, $C_1$–$C_4$alkyl or $C_1$–$C_4$alkylcarbonyl;

$R_{31}$, $R_{32}$, $R_{33}$ and $R_{34}$ are each independently of the other hydrogen or $C_1$–$C_4$alkyl, or $R_{31}$ and $R_{32}$ or $R_{33}$ and $R_{34}$, together with the carbon atom to which they are bonded, form a 3 to 7-membered ring which may contain one or two oxygen atoms or a group $NR_{36}$, wherein $R_{38}$ A is hydrogen or $C_1$–$C_4$alkyl;

$Y_2$ is oxygen, —NH—, a group

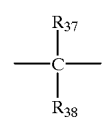

or a group

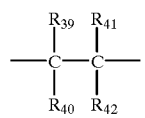

$R_{37}$ and $R_{38}$ are each independently of the other hydrogen or $C_1$–$C_4$alkyl; or $R_{37}$ and $R_{38}$, together with the carbon atom to which they are bonded, form a 3- to 7-mnembered ring which may contain one or two oxygen atoms or a group $NR_{35}$, wherein $R_{35}$ is hydrogen, $C_1$–$C_4$alkyl or $C_1$–$C_4$alkycarbonyl;

$R_{39}$, $R_{40}$, $R_{41}$ and $R_{42}$ are each Independenty of the others hydrogen or $C_1$–$C_4$alkyl, or $R_{39}$ and $R_{40}$ or $R_{41}$ and $R_{42}$, together with the carbon atom to which they are bonded, form a 3- to 7-membered ring which may contain one or two oxygen atoms or a group $NR_{43}$, wherein $R_{43}$ Is hydrogen or $C_1$–$C_4$alkyl;

Z is a group

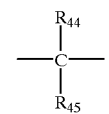

or a group

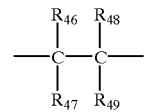

$R_{44}$, $R_{45}$, $R_{46}$, $R_{47}$, $R_{48}$ and $R_{49}$ are each independently of the others hydrogen or methyl;

p is 0 or 1;

$R_{50}$ is hydrogen or halogen; and $R_{51}$ is hydrogen, halogen, methyl, difluoromethoxy, trifluoromerhoxy or cyano.

\* \* \* \* \*